(12) United States Patent
Coulombe et al.

(10) Patent No.: US 11,701,159 B2
(45) Date of Patent: Jul. 18, 2023

(54) MRI-COMPATIBLE CRYOCATHETERS AND SYSTEM

(71) Applicant: Medtronic CryoCath LP, Toronto (CA)

(72) Inventors: Nicolas Coulombe, Anjou (CA); Ioana Deac, Vaudreuil-Dorion (CA); John B. Horrigan, Beverly, MA (US); Jean-Pierre Lalonde, Candiac (CA); Dan Wittenberger, L'Ile Bizard (CA)

(73) Assignee: Medtronic CryoCath LP, Toronto (CA)

(*) Notice: Subject to any disclaimer, the term of this patent is extended or adjusted under 35 U.S.C. 154(b) by 408 days.

(21) Appl. No.: 15/495,281

(22) Filed: Apr. 24, 2017

(65) Prior Publication Data

US 2018/0064481 A1 Mar. 8, 2018

Related U.S. Application Data

(60) Provisional application No. 62/383,028, filed on Sep. 2, 2016.

(51) Int. Cl.
*A61B 18/02* (2006.01)
*A61B 5/01* (2006.01)
(Continued)

(52) U.S. Cl.
CPC ........... *A61B 18/02* (2013.01); *A61B 5/01* (2013.01); *A61B 5/02154* (2013.01);
(Continued)

(58) Field of Classification Search
CPC ....... A61B 18/02; A61B 5/01; A61B 5/02154; A61B 5/02055; A61B 2018/0022;
(Continued)

(56) References Cited

U.S. PATENT DOCUMENTS 6,213,974 B1* 4/2001 Smith ............... A61M 25/0136
600/139
7,063,682 B1* 6/2006 Whayne ........... A61M 25/0043
600/146
(Continued)

OTHER PUBLICATIONS

Kholmovski, Eugene G., Ph.D et al., Real-Time MRI-Guided Cardiac Cryo-Abation: A Feasibility Study, J Cardiovasc Electrophysiol, vol. 27, pp. 602-608, May 2016.
(Continued)

*Primary Examiner* — Eun Hwa Kim
*Assistant Examiner* — Catherine Premraj
(74) *Attorney, Agent, or Firm* — Michael Best & Friedrich LLP

(57) ABSTRACT

A system and device for cryoablation of tissue that is suitable for use within an MRI environment. The device may include an elongate body, a treatment element at the distal portion of the elongate body, and one or more pull fibers. The pull fibers may be composed of a non-ferromagnetic material, such as a polymer. Likewise, none of the other device components may be composed of a ferromagnetic material. The device may also include at least one fiber optic sensor. The elongate body distal portion may include a distal tip to which the pull fibers are directly coupled. Additionally or alternatively, the elongate body may include one or more pull fiber lumens configured to allow the pull fibers to deflect the distal portion when a pull force is exerted on the pull fibers.

20 Claims, 9 Drawing Sheets

(51) Int. Cl.
*A61B 5/0215* (2006.01)
*A61M 25/01* (2006.01)
*A61B 18/00* (2006.01)
*A61B 5/0205* (2006.01)
*A61B 17/00* (2006.01)
*A61M 25/00* (2006.01)

(52) U.S. Cl.
CPC . *A61B 5/02055* (2013.01); *A61B 2017/00911* (2013.01); *A61B 2018/00255* (2013.01); *A61B 2018/00577* (2013.01); *A61B 2018/00791* (2013.01); *A61B 2018/0212* (2013.01); *A61B 2018/0262* (2013.01); *A61B 2505/05* (2013.01); *A61B 2562/0233* (2013.01); *A61M 25/0074* (2013.01); *A61M 25/0147* (2013.01); *A61M 2205/05* (2013.01)

(58) Field of Classification Search
CPC ........... A61B 2018/00255; A61B 2018/00285; A61B 2018/00577; A61B 2018/0212; A61B 2018/0262; A61B 2505/05; A61B 2562/0233; A61B 2018/00791; A61B 2017/00911; A61M 25/0023; A61M 25/0147; A61M 25/09; A61M 2025/0166; A61M 2205/05; A61M 25/0074
See application file for complete search history.

(56) References Cited

U.S. PATENT DOCUMENTS

| | | | | |
|---|---|---|---|---|
| 2006/0135961 | A1* | 6/2006 | Rosenman | A61M 25/0045 606/108 |
| 2007/0156133 | A1* | 7/2007 | McDaniel | A61M 25/00 606/41 |
| 2009/0118723 | A1* | 5/2009 | Lalonde | A61B 18/02 606/21 |
| 2011/0270173 | A1* | 11/2011 | Gibson | A61M 25/0041 604/95.04 |
| 2013/0012777 | A1* | 1/2013 | Baum | A61B 1/00013 600/110 |
| 2013/0131593 | A1* | 5/2013 | Selkee | A61M 25/09 604/95.04 |
| 2015/0141987 | A1* | 5/2015 | Caplan | A61B 18/1492 606/41 |
| 2015/0366435 | A1* | 12/2015 | Williams | A61B 1/0052 600/149 |
| 2016/0235477 | A1* | 8/2016 | Satake | A61B 18/1492 |
| 2017/0189644 | A1* | 7/2017 | Fischer, Jr. | A61M 25/10 |

OTHER PUBLICATIONS

Kholmovski, Eugene G., Real-time Guided Cardiac Cryo-ablation, UCAIR, Department of Radiology, University of Utah, Salt Lake City, Utah, United States, CARMA Center, University of Utah, Salt Lake City, Utah, United States, Medtronic CryoCath, Montreal, Quebec, Canada.

* cited by examiner

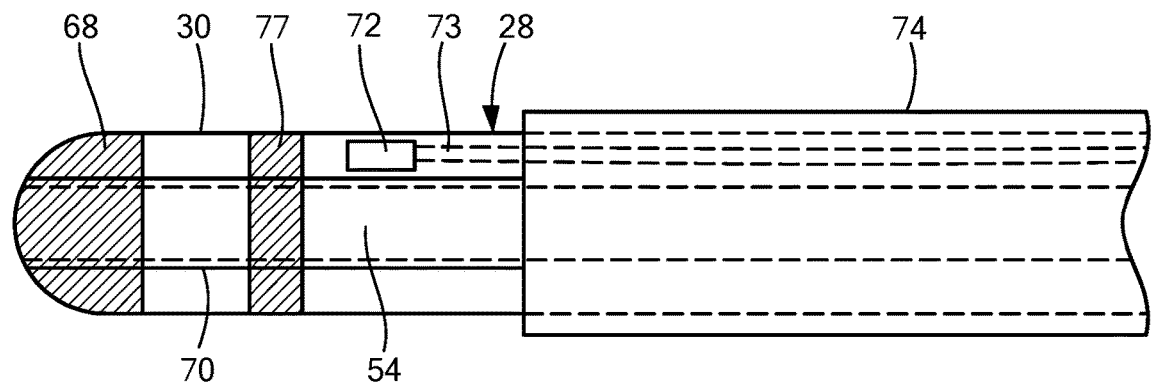
*FIG. 2*
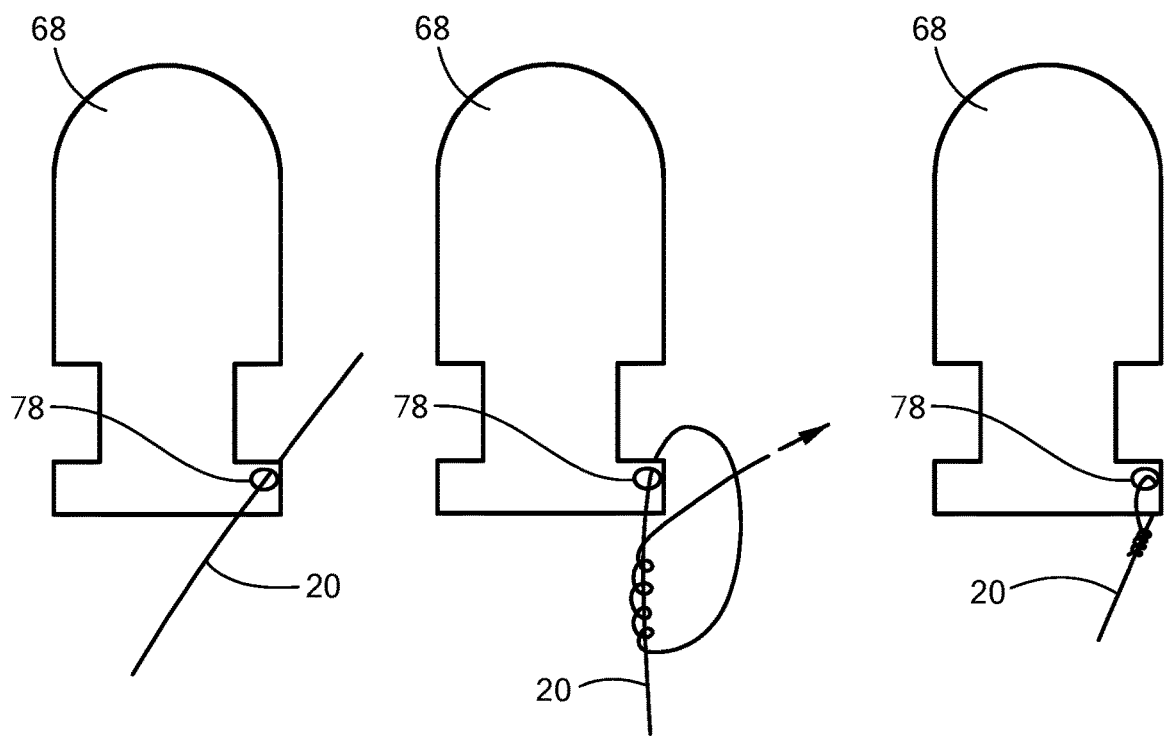
*FIG. 3A*  *FIG. 3B*  *FIG. 3C*

MRI-COMPATIBLE CRYOCATHETERS AND SYSTEM

CROSS-REFERENCE TO RELATED APPLICATION

This application is related to and claims priority to U.S. Provisional Patent Application Ser. No. 62/383,028, filed Sep. 2, 2016, entitled MRI-COMPATIBLE CRYOCATHETERS AND SYSTEM, the entirety of which is incorporated herein by reference.

STATEMENT REGARDING FEDERALLY SPONSORED RESEARCH OR DEVELOPMENT n/a

TECHNICAL FIELD

The present invention relates to devices and systems for performing a medical procedure that are compatible for use with MRI systems.

BACKGROUND

Cardiac cryoablation is commonly used for the treatment of cardiac conditions, such as atrial fibrillation and ventricular tachycardia. The success of this procedure largely depends on lesion quality, including the permanency and continuity of the lesions created. Additionally, damage to non-target tissue may be difficult to prevent. However, it may be challenging to evaluate lesion quality and collateral damage using electrophysiological measurements. X-ray methods may be used for visualization of the lesion, but this exposes the patient to radiation.

Magnetic resonance imaging (MRI) is often used to image soft tissues. Its ability to provide three-dimensional representations of cardiac tissue scarring can facilitate understanding of cardiac diseases that may result in arrhythmia, and ultimately help enhance ablation effectiveness. Other notable benefits include the possibility of tracking device navigation within the heart without fluoroscopy and visualizing the effect of ablation on tissue in real time, ensuring contiguous lesion sets while avoiding collateral injury. Also, the ability of MRI to distinguish between normal myocardium, fibrotic tissue, and adipose tissue could help in identifying treatment target areas and navigating to them.

However, most currently known ablation devices are not suitable for use within an MRI magnetic environment. Focal radiofrequency catheters that are MRI compatible are currently being developed, but these may be less than ideal because they are complex, difficult to track in an MRI environment, and may still require long procedure times. The popularity of cryoablation for atrial fibrillation is quickly increasing, and the technique has shown to be successful in the creation of endocardial lesions within an MRI system. Using MRI, navigation to the anatomical targets, such as pulmonary veins, can be visualized. Additionally, the formation of ice during cryoablation can be seen with MRI so that the operator can assess its extent and contiguity while avoiding ablation of collateral structures. Further, cryoablation may create less post-ablation edema, which may lead to better outcomes with a lower change of post-ablation gap.

SUMMARY

The present Application advantageously provides devices and systems for performing a medical procedure, namely, cryoablation devices and systems that are compatible for use with MRI systems. In one embodiment, an MRI-compatible medical device includes an elongate body including a proximal portion and a distal portion, a treatment element at the distal end of the elongate body, and a non-ferromagnetic pull fiber coupled to the elongate body distal portion.

In one aspect of the embodiment, the elongate body further includes a first pull fiber lumen, a second pull fiber lumen, and a main lumen. In one aspect of the embodiment, the elongate body further includes a longitudinal axis, the main lumen being coaxial with the longitudinal axis and the first and second pull fiber lumens being diametrically opposite each other and at least substantially parallel to the central lumen. In one aspect of the embodiment, the elongate body further includes a connecting lumen that is in communication with each of the first and second pull fiber lumens, the connecting lumen lying in a plane that is substantially orthogonal to the longitudinal axis.

In one aspect of the embodiment, the connecting lumen is curved around the main lumen.

In one aspect of the embodiment, the connecting lumen is curved around the main lumen in a semicircular shape.

In one aspect of the embodiment, the connecting lumen is curved around the main lumen in a spiral shape.

In one aspect of the embodiment, the connecting lumen is a first connecting lumen, the elongate body further including a second connecting lumen, the first connecting lumen having a semicircular shape that extends in a first direction and the second connecting lumen having a second semicircular shape that extends in a second direction opposite the first direction.

In one aspect of the embodiment, the pull fiber is composed of a polymer.

In one aspect of the embodiment, the medical device further comprising at least one fiber optic sensor.

In one aspect of the embodiment, the at least one fiber optic sensor is located on a lateral surface of the elongate body.

In one aspect of the embodiment, the treatment element is an expandable element, the medical device further comprising a shaft at least partially disposed within the expandable element.

In one aspect of the embodiment, the at least one fiber optic sensor is located on the shaft within the expandable element.

In one aspect of the embodiment, the medical device further comprising an optical multiplexer in communication with the at least one fiber optic sensor.

In one aspect of the embodiment, the medical device further comprising a deflection mechanism coupled to the non-ferromagnetic pull fiber, the deflection mechanism including: a first face; a second face opposite the first face; a rounded lateral wall between the first and second faces, the rounded lateral wall defining a circumference of the deflection mechanism; a central hole extending through the first and second faces; a pin hole that extends through the lateral surface to the central hole; a pull fiber channel within the rounded lateral wall, the pull fiber channel being sized and configured to accept at least a portion of the non-ferromagnetic pull fiber; and a pin removably insertable within the pin hole.

In one embodiment, an MRI-compatible medical device includes: an elongate body including a proximal portion, a distal portion, a longitudinal axis, a main lumen that is coaxial with the longitudinal axis, a first pull fiber lumen that is parallel to the longitudinal axis, a second pull fiber lumen that is parallel to the longitudinal axis, and a connecting lumen that lies in a plane that is at least substantially orthogonal to the longitudinal axis, the first and second pull fiber lumens being diametrically opposite each other, the main lumen being between the first and second pull fiber lumens; a treatment element at the distal end of the elongate body; a non-ferromagnetic pull fiber located within each of the first and second pull fiber lumens; a handle at the proximal end of the elongate body; and a deflection mechanism located within handle and coupled to the pull fiber, the deflection mechanism including a first face, a second face, a rounded lateral wall between the first and second faces, a central hole that extends through the first and second faces, and a pin hole that extends through the lateral surface to the central hole.

In one embodiment, an MRI-compatible medical system includes: a medical device including: an elongate body having a proximal portion and a distal portion; a treatment element at the distal end of the elongate body; a non-ferromagnetic pull fiber coupled to the elongate body distal portion; a handle coupled to the elongate body proximal portion; at least one pull fiber lumen within the elongate body; and at least one fiber optic sensor; and a console including: at least one processor in fluid and optical communication with the medical device, the medical device not being in electrical communication with the console.

In one aspect of the embodiment, the handle has an optic multiplexer in optic communication with the at least one fiber optic sensor; and the console includes an optic demultiplexer in communication with the optic multiplexer.

In one aspect of the embodiment, the elongate body distal portion has a distal tip, the non-ferromagnetic pull fiber being coupled to the distal tip.

In one aspect of the embodiment, the elongate body further has: a longitudinal axis; a main lumen that is coaxial with the longitudinal axis; a first pull fiber lumen that is at least substantially parallel to the longitudinal axis; a second pull fiber lumen that is diametrically opposite the first pull fiber lumen and is at least substantially parallel to the longitudinal axis; and a connecting lumen that is in communication with each of the first and second pull fiber lumens, the connecting lumen lying in a plane that is substantially orthogonal to the longitudinal axis.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 shows a cross-sectional view of a focal catheter that may be used with the system of FIG. 1;

FIGS. 3A-3C show a first configuration for fastening pull fibers to a distal tip of an MRI-compatible medical device;

DETAILED DESCRIPTION

Figure 1:
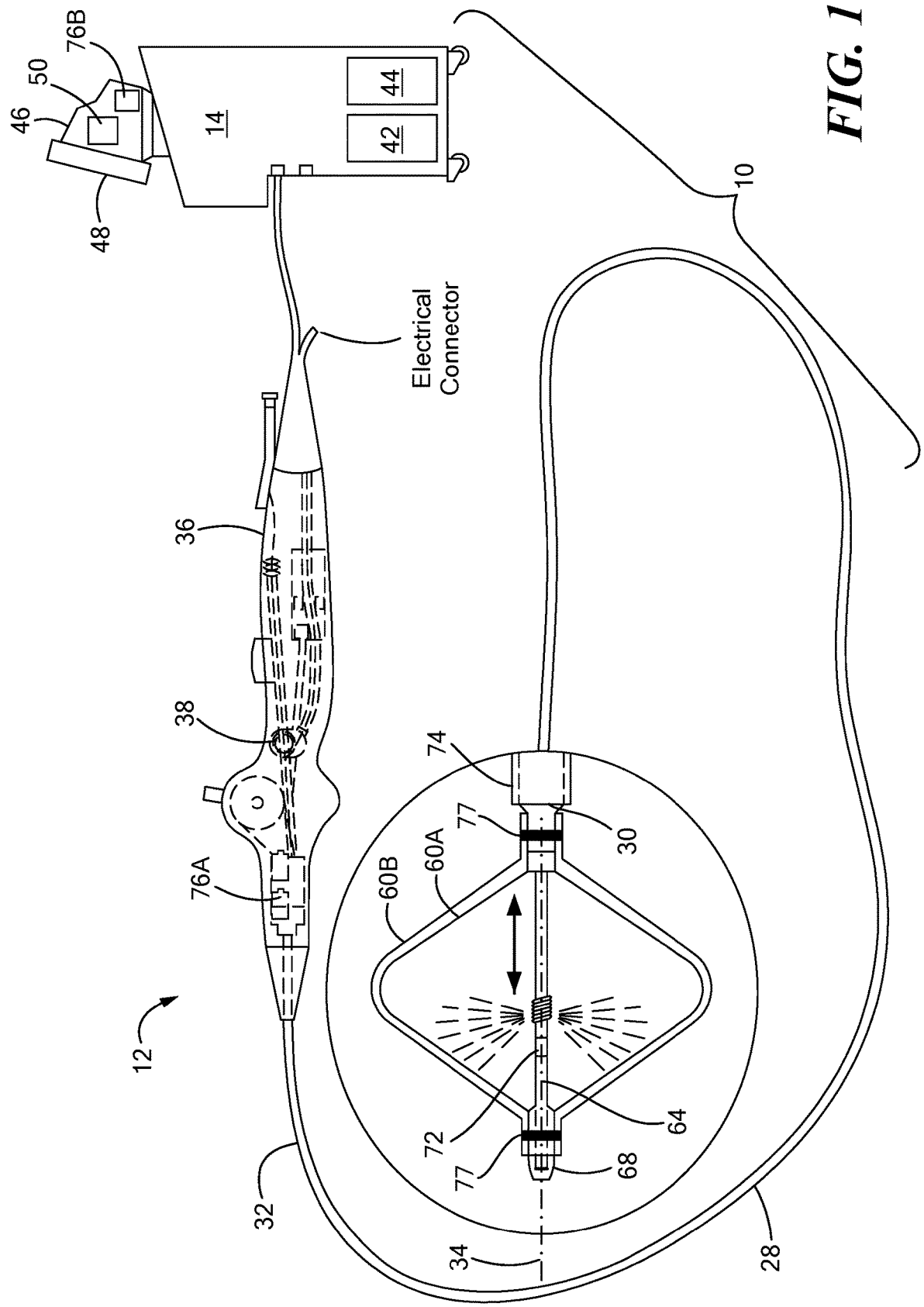
FIG. 1 shows an exemplary cryoablation system with cryoablation device suitable for use with an MRI system, the cryoablation device being a balloon catheter.

The devices, systems, and methods described herein may be used to perform cryoablation or other tissue treatment in combination with an MRI system without causing interference. Before describing in detail exemplary embodiments, it is noted the device, system, and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Referring now to the drawings in which like reference designations refer to like elements, an exemplary MRI-compatible cryoablation system is shown in FIG. 1. The system 10 may generally include a medical device 12 (for example, an ablation, treatment, and/or mapping catheter) and a console 14. The medical device 12 may include one or more pull fibers 20 for causing deflection of a distal portion of the device 12 during steering and navigation. The device 12 may be MRI compatible, meaning that the device 12 will function normally in and will not be damaged by the MRI environment, and will not create magnetic resonance image artifacts that would impede the visualization of the treatment effects on tissue.

The medical device 12 may include an elongate body 28 having a distal portion 30, a proximal portion 32, a longitudinal axis 34, and one or more lumens extending between the distal portion 30 and the proximal portion 32. The distal portion 30 of the elongate body 28 may be capable of in-plane and/or out-of-plane deflection and is steerable by actuation of the one or more pull fibers 20. The proximal portion 32 of the elongate body 28 may be affixed to a handle 36, which may have various inlets, outlets, steering control mechanisms (for example, knobs, toggles, etc.), and/or other components. The proximal portion of the handle 36 may include a coaxial fitting or connector for connecting the device 12 to the console 14 for, for example, refrigerant delivery and recovery. However, the handle may not include an electrical fitting or connector if the device 12 does not include electrical components. If the handle was manufactured to include an electrical fitting or connector, that conduit may be cut and blocked, such as with a DYMAX® gel (Dymax Corporation, Connecticut) or similar (as shown in FIG. 1). Put another way, the device 12 may not be in electrical communication with the console 14.

The one or more pull fibers 20 may be either coupled to or routed through the handle 36. For example, the one or more pull fibers 20 may be secured to and/or wound around a rotatable deflection mechanism 38, such as a spool (shown in FIG. 13A) that is coupled to, proximate, or within the handle 36 in order to exert a pull force on the one or more pull fibers and thereby cause deflection of a distal portion of the elongate body 28. The term "pull fiber" is used herein to refer to a cord or fiber that is used similarly to or in the same way as a typical pull wire, but that contains no ferromagnetic materials that would interfere with an MRI magnet. As is discussed in greater detail below, the one or more pull fibers 20 may be composed of one or more polymers, such as aramides (aromatic polyamides), or high-strength nylons or polyesters.

The medical device 12 may be in fluid, mechanical, and/or electrical communication with the console 14. For example, the system 10 and device 12 may be configured for use with any of a variety of energy modalities (such as cryotreatment, radiofrequency energy, laser energy, pulsed field energy, microwave energy, ultrasound, energy or the like), for mapping tissue, and/or any other medical procedure that is facilitated by using a steerable catheter. As such, the console 14 may include one or more components appropriate for the purpose of the system. As shown in FIG. 1, the device 12 and system 10 may be configured for cryoablation and, therefore, the console 14 may include a refrigerant reservoir 42 and a refrigerant recovery reservoir 44. The console 14 may further include a computer 46 having a display 48 and one or more processors 50 for receiving and processing data from the system 10, and/or various user control devices (for example, buttons, knobs, valves, keyboard, touch screen, foot pedals, etc.).

The elongate body may include a plurality of lumens. For example, the elongate body 28 may include a main lumen 54 and at least one pull fiber lumen. In one embodiment, the elongate body 28 may include a first pull fiber lumen 56A, a second pull fiber lumen 56B, and a connecting lumen 58 (as shown in FIGS. 5-11). Alternatively, the elongate body 28 may include a main lumen 54 and a single pull fiber lumen 56 for all of the one or more pull fibers 20. However, it will be understood that more or fewer lumens that shown and described herein may be used, depending on the device components and other design considerations. The pull fiber lumens may be configured to allow the pull fibers 20 to deflect the elongate body distal portion in at least one direction 30 when a pull force is exerted on the pull fibers 20, as discussed in more detail below.

The device 12 may include one or more treatment elements. As shown in to FIG. 1, the medical device may have at least one expandable treatment element 60. For example, the treatment element may be one or more balloons 60. As a non-limiting example, the device 12 shown in FIG. 1 may be similar to the ARCTIC FRONT® or ARCTIC FRONT ADVANCE® (Medtronic CryoCath LP Limited Partnership Canada, CA) devices. The one or more balloons 60 may be coupled to or disposed on at least a portion of the distal portion 30 of the elongate body 28. For example, the one or more balloons 60 may include an inner balloon 60A and an outer balloon 60B. Refrigerant may be injected from the refrigerant reservoir 42, through one or more fluid injection elements 62, and into an interstitial space between the inner 60A and outer 60B balloons and/or into an expansion chamber defined by the inner balloon 60A.

The device 12 may include a shaft 64 that is disposed within the elongate body 28, such as within the main lumen 54 of the elongate body 28. In embodiments wherein the shape of the treatment element 60 is adjustable, the shaft 64 may be slidably disposed within the main lumen 54. Further, the shaft 64 may itself define a lumen through which a mapping device, guide wire, or other device may be advanced, and may define or include a distal tip 68 that may be the distalmost end of the device (for example, the distal tip 68 may define a distal "nose" of the device). Although not shown, the device 12 may further include one or more refrigerant delivery lumens in fluid communication with a refrigerant reservoir 42, a fluid injection element, and one or more refrigerant exhaust lumens in fluid communication with the refrigerant recovery reservoir 44. Each of the one or more refrigerant delivery and exhaust lumens may also be in fluid communication with the treatment element 60.

Figure 6:
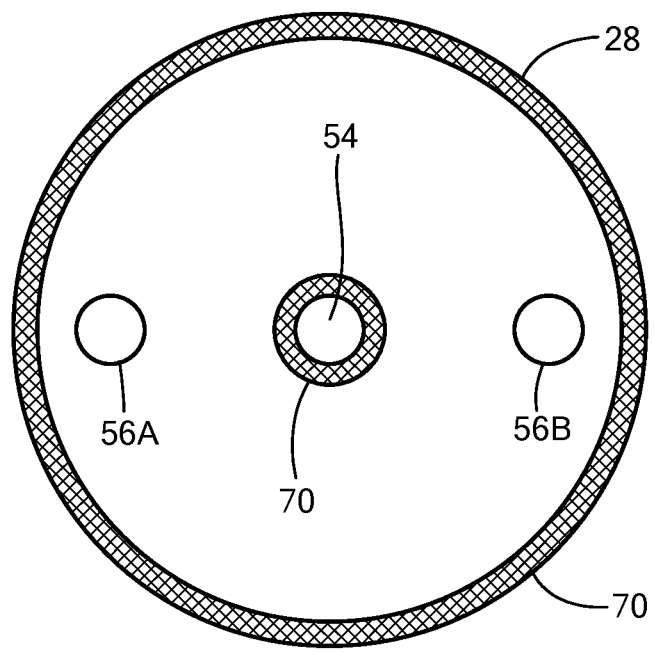
FIG. 6-11 show cross-sectional views of a distal portion having variations of a third configuration for fasting pull fibers to a distal end of an MRI-compatible medical device.
Figure 7:
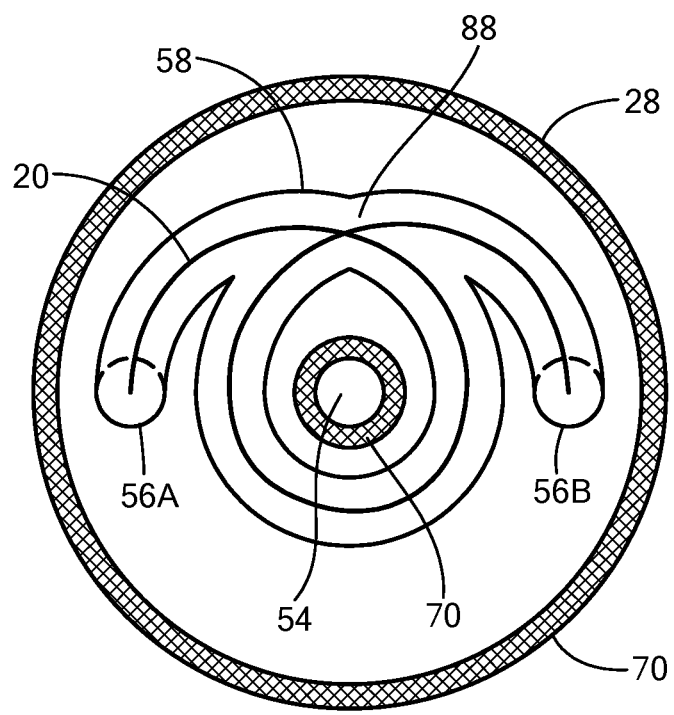
Figure 11:
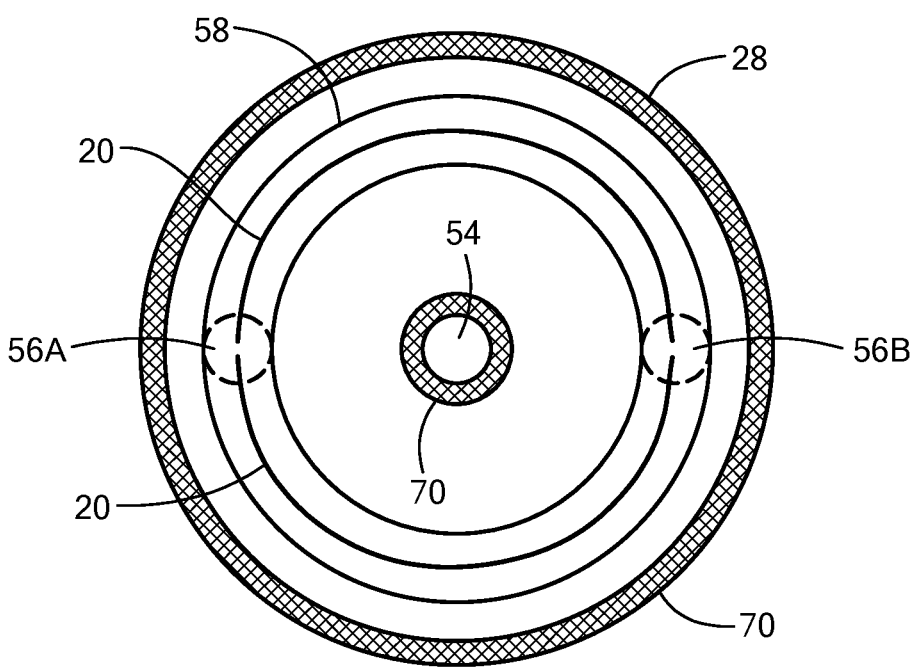
Figure 12:
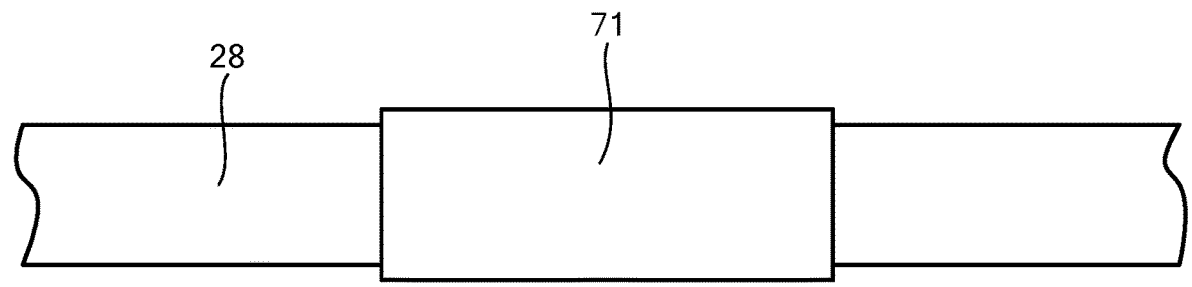
FIG. 12 shows a portion of an elongate body of the medical device around which heatshrink material has been applied.

Although the MRI-compatible device 12 may include some metal components, the device 12 does not include any ferromagnetic components or conductors that would interfere with the MRI system. As a non-limiting example, the device elongate body 28 may be composed of a polymer, such as PEBAX® (Arkema France Corporation, France), nylons, urethanes, or the like, and/or combinations thereof. The elongate body 28 may also include a braided polymer layer 70 lining, and a similar braided layer 70 may line one or more of the lumens, such as the main lumen 54. The braided layer(s) 70 may include any suitable braid configuration, may include polymer fibers of varying size and shape, and may have a varied braid density per inch crossings (PIC) to achieve the desired final physical properties of the device. The elongate body 28 and main lumen 54 are shown in FIGS. 6 and 7 has each having a braided layer 70. The braided layers 70 are not shown in FIGS. 8-11 for simplicity, although it will be understood that the elongate body 28 and lumens (including the main lumen 54) may include braided or other layers 70. Additionally or alternatively, the main lumen 54 may include a non-braided polymer that is stiffer than the polymer from which the elongate body 28 is composed, such as polyetheretherketone (PEEK) tubing. Further, the one or more refrigerant delivery and exhaust lumens may be defined by a polymer tubing, such as polyimide. Additionally, at least a portion of the elongate body 28 may include a thicker wall or outer layer of material such as heatshrink tubing 71 to prevent kinking (as shown in FIG. 12). For example, the heatshrink tubing 71 may be placed at a curvature point for steerability or other areas prone to kinking, such as near the strain relief. Additionally or alternatively, the heatshrink tubing 71 may be placed at or near the distal vacuum restriction. The device 12 may include one or more electrodes, but any electrodes on the device 12 are composed of non-ferromagnetic metals. Although non-ferromagnetic metals are not attracted by the MRI magnet, they may still disturb the radiofrequency field, create artifacts, and generate heat because of the Foucault current that circulate within. Therefore, it will be understood that reference herein to "non-ferromagnetic metals" that are suitable for use in the device and system described herein are those non-ferromagnetic metals that are not attracted by the MRI magnet and which generate acceptable heat (<40° C. IHMO) and signal noise (distortion/abheration/artifacts) to the radiofrequency fields.

Additionally, the device 12 may not include thermocouples or other sensors that include ferromagnetic components. However, the device 12 may include one or more fiber optic sensors, such as a fiber optic temperature sensor and/or a fiber optic pressure sensor 72, in which case the elongate body 28 may include one or more dedicated lumens for the fiber optic components (for example, the fiber optic lumen 73 as shown in FIG. 2), or they may be located within other lumens or within or coupled to other device components. Further, the one or more fiber optic temperature and pressure sensors 72 may be combined for use as a single fiber optic fiber, with an optical multiplexer 76A and optical demultiplexer 76B within the handle 36 and/or console 14 (for example, within the computer 46) to rapidly alternate between the two types of measurements. As a non-limiting example, the fiber optic sensor 72 may be affixed to the shaft 64 within the treatment element 60. This may allow for measurement of a temperature and/or pressure within the treatment element 60, which may be useful for pressure-controlled refrigerant delivery and/or as a safety system to ensure there are no breaches within the treatment element when combined with console injection pressure and return flow measurements. Alternatively, non-ferromagnetic thermocouples like Platinum/Paladium (Pt/Pd) or Platinum-Rhodium/Platinum (Pt—Rh Pt) can also be used. Additionally or alternatively, the fiber optic sensor 72 may be located on an external lateral surface of the elongate body 28.

The MRI-compatible device 12 may further include one or more non-ferromagnetic components to allow for catheter tracking and navigation control. For example, the device 12 may include one or more passive markers 77 made of paramagnetic or weakly ferromagnetic material or doped polymer that creates an artifact that can be seen using MRI, or active coils.

The device 12 may also include one or more non-ferromagnetic pull fibers 20 for steering and navigating the device to a target treatment site. The pull fibers 20 are similar to or the same in function as traditional pull wires, but are referred to as "pull fibers" because they do not contain ferromagnetic materials that would interfere with an MRI magnet. As a non-limiting example, the pull fibers 20 may be composed of aramides, such as KEVLAR® (E. I. Du Pont de Nemours and Company, Delaware, US), or high-strength, low-elongation nylons or polyesters. The pull fibers 20 may be attached, coupled, or otherwise in mechanical communication with the elongate body distal portion 30, such as shown and described in FIGS. 3A-11. For example, the pull fibers 20 may be coupled to at least a portion of the distal tip 68. At least a portion of the distal tip 68 may be exposed distally beyond the elongate body 28, with the pull fibers 20 being completely within the elongate body 28, such as in one or more elongate body lumens. If the treatment element is an expandable element as shown in FIG. 1, the pull fibers 20 may be completely within the expandable element 60 and/or the elongate body 28.

As is shown in FIGS. 1 and 2, the device 12 may be delivered to a treatment site using a delivery sheath 74 that is also MRI compatible. For example, the sheath 74 may be composed of a braided polymer, include a polymer or non-ferromagnetic pull-fiber ring or attachment mechanism, and/or non-ferromagnetic pull fibers, such as polymer pull fibers. For example, the pull fibers 20 may be composed of a polymer, such as an aramide like KEVLAR® (E. I. Du Pont de Nemours and Company, Delaware, US), or high-strength nylons and/or polyesters.

Referring now to FIG. 2, a focal-catheter-type medical device (that is, a device without an expandable element) is shown. As a non-limiting example, the device 12 shown in FIG. 2 may be similar to the FREEZOR® (Medtronic Cryocath LP Limited Partnership Canada, CA), FREEZOR® Xtra, or FREEZOR® MAX devices. Like the balloon catheter described above, the device shown in FIG. 2 does not contain any ferromagnetic components that would significantly interact with an MRI magnet or radiofrequency fields. Also like the device shown in FIG. 1, the device shown in FIG. 2 may include an elongate body 28 may be composed of a polymer, such as PEBAX®, nylons, urethanes, or the like, and/or combinations thereof. The elongate body 28 may also include a braided polymer layer 70 lining, and a similar braided layer 70 may line one or more of the lumens, such as the main lumen 54. The braided layer 70 may include any suitable braid configuration, may include polymer fibers of varying size and shape, and may have a varied braid density per inch crossings (PIC) to achieve the desired final physical properties of the device. Additionally or alternatively, the main lumen 54 may include a non-braided polymer that is stiffer than the polymer from which the elongate body 28 is composed, such as polyetheretherketone (PEEK) tubing. Further, the one or more refrigerant delivery and exhaust lumens may be defined by a polymer tubing, such as polyimide. The device 12 may include one or more electrodes, but any electrodes on the device 12 are composed of non-ferromagnetic metals. Additionally, the device 12 may include a distal tip 68 that is conductive (for example, an electrode) or nonconductive and which defines the distalmost end of the device. Unlike the device 12 shown in FIG. 1, the device 12 shown in FIG. 2 does not include an expandable element or component.

Additionally, the device 12 of FIG. 2 may include one or more fiber optic sensors, such as a fiber optic temperature sensor and/or a fiber optic pressure sensor 72, as described above. Further, the device 12 may include one or more navigation markers 77 as described above, and may be delivered to a target treatment site using a delivery sheath 74 described above.

Referring now to FIGS. 3A-11, various configurations for fasting pull fibers to a distal portion of the device are shown. In the configuration shown in FIGS. 3A-3C, the distal tip 68 of the device 12 may include an aperture or passage 78 through which a distal portion of a pull fiber may pass (as shown in FIG. 3A). The distal portion of the pull fiber may then be knotted (as shown in FIG. 3B) such that the pull fiber cannot be pulled from the aperture or passage 78 of the distal tip 68 (as shown in FIG. 3C). As a non-limiting example, a uni knot, surgeon's knot, or similar knot may be used. Additionally or alternatively, one or more non-ferromagnetic mechanical coupling devices or other coupling methods may be used, such as clips, rings, wraps, chemical adhesives, laser welding, or the like.

Figure 4A:
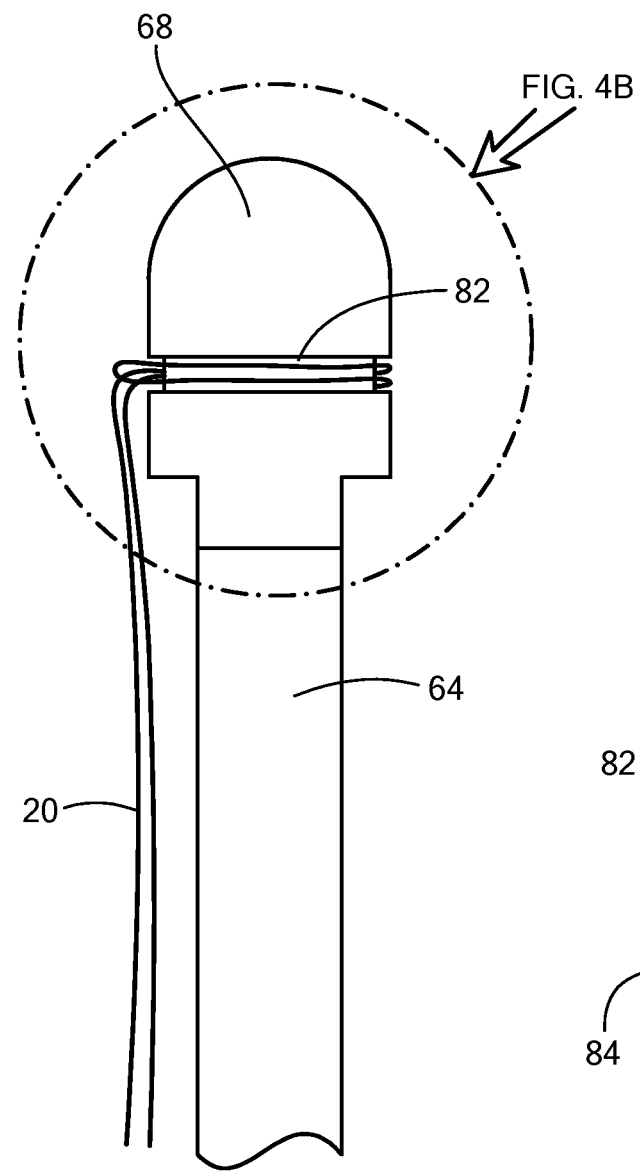
FIGS. 4A and 4B show a second configuration for fasting pull fibers to the distal tip of an MRI-compatible medical device.
Figure 4B:
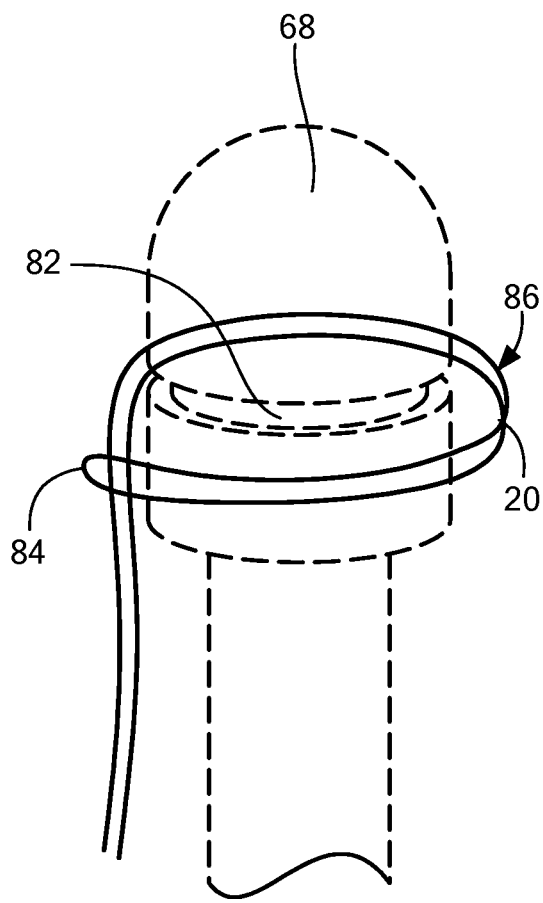

In the configuration shown in FIGS. 4A and 4B, the distal tip 68 or a distal portion of the shaft 64 may include a groove or notch 82 at least partially surrounding the circumference of the distal tip 68 or shaft 64. The groove or notch 82 may have a width and depth that is sufficient to receive at least one pull fiber 20, thus securing the one or more pull fibers 20 to the distal end of the device. In the non-limiting embodiment shown in FIGS. 4A and 4B, one length of pull fiber 20 may be secured to the distal tip 68 by a lark's head knot or similar to create two pull fibers 20A, 20B that may be manipulated independently of each other to steer the device 12. The single length of pull fiber 20 may be folded in half at a fold point 84, with the ends of the pull fiber 20 being passed through the fold point 84 to create a loop 86 that passes around the distal tip 68 within the groove or notch 82 (as is shown in detail in FIG. 4B). The distal tip 68 and notch 82 is shown in dashed lines in FIG. 4B so the pull fiber 20 can be clearly seen.

Figure 5:
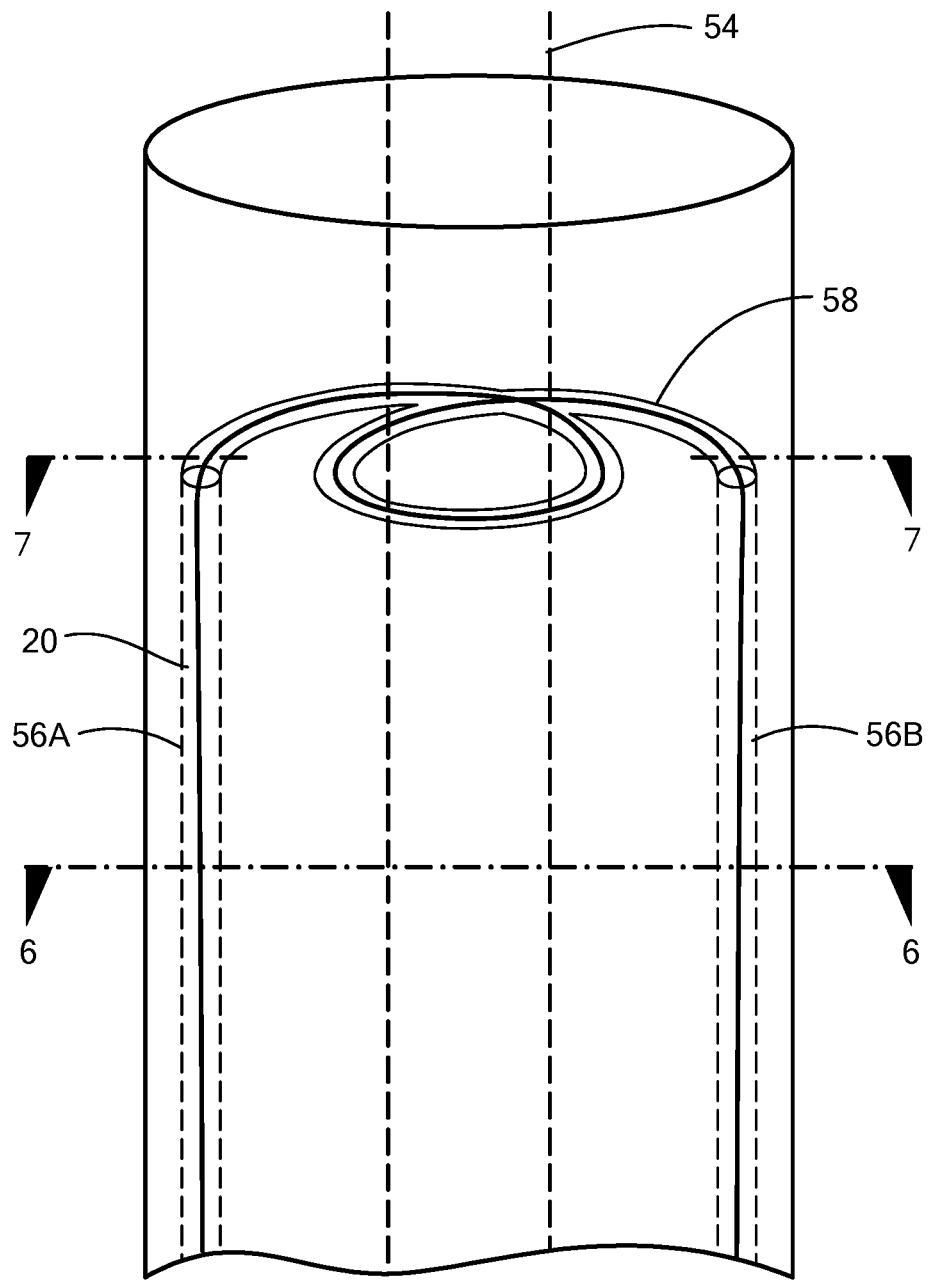
FIG. 5 shows a cross-sectional view of an exemplary elongate body of a cryoablation device of FIGS. 1-3.

In the configuration shown in FIGS. 5-11, the pull fibers 20 may be able to transmit a pull force on the distal portion of the device 12 without being physically coupled to the elongate body 28. As shown in FIGS. 5-11, the distal portion 30 of the device may include a first pull fiber lumen 56A, a second pull fiber lumen 56B, and a connecting lumen 58. The first 56A and second 56B pull fiber lumens may be at least substantially parallel to the longitudinal axis 34 of the elongate body 28 and may be diametrically opposite each other, on either side of the main lumen 54. In other words, each of the first 56A and second 56B pull fiber lumens may be radially offset from the longitudinal axis 34. The main lumen 54 may lie in the center of the elongate body 28, coaxial with the elongate body longitudinal axis 34. The connecting lumen 58 may generally lie in a plane that is at least substantially orthogonal to the longitudinal axis 34 of the elongate body 28, and may be curved to form a circle, loop, or semicircle around the main lumen 54 through which a pull fiber 20 may pass (as shown in FIGS. 5 and 6. The cross-sectional view in FIG. 6 is taken along line 6-6 in FIG. 5). For example, a single pull fiber 20 may be used and may be passed through the first pull fiber lumen 56A toward the distal portion 30 of the elongate body. Once at the distal end of the first pull fiber lumen 56A, the pull fiber 20 may then pass into the connecting lumen 58, which at least partially encircles the main lumen 54. Once the pull fiber 20 has passed through the connecting lumen 58 around the main lumen 54, the pull fiber 20 may then pass into the second pull fiber lumen 56B and toward the proximal portion 32 of the elongate body 28. Thus, the elongate body 28 may be deflected or otherwise manipulated by actuation of the pull fibers 20, even though the pull fiber 20 is not physically coupled to the distal portion of the device. For example, friction between the pull fiber 20 and the material of the lumens 56A, 56B, 58 may be enough to keep the pull fiber 20 within and exerting force against the connecting lumen 58 and, therefore, the distal end of the device. Additionally, a proximal portion of one of the pull fibers 20 may be affixed to an anchor point within the handle, for example, and the proximal portion of the other one of the pull fibers 20 may be coupled to a deflection actuator mechanism (such as the one shown and described in FIGS. 13A and 13B).

Figure 8:
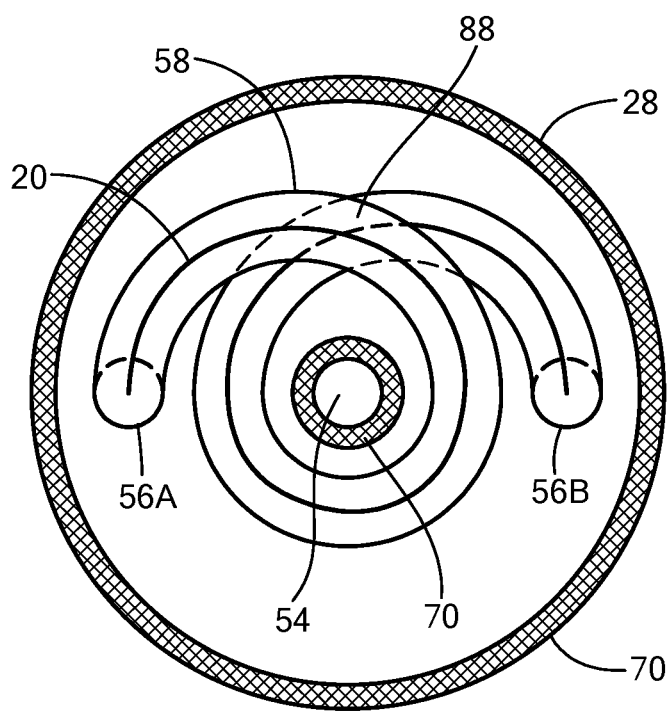
Figure 9:
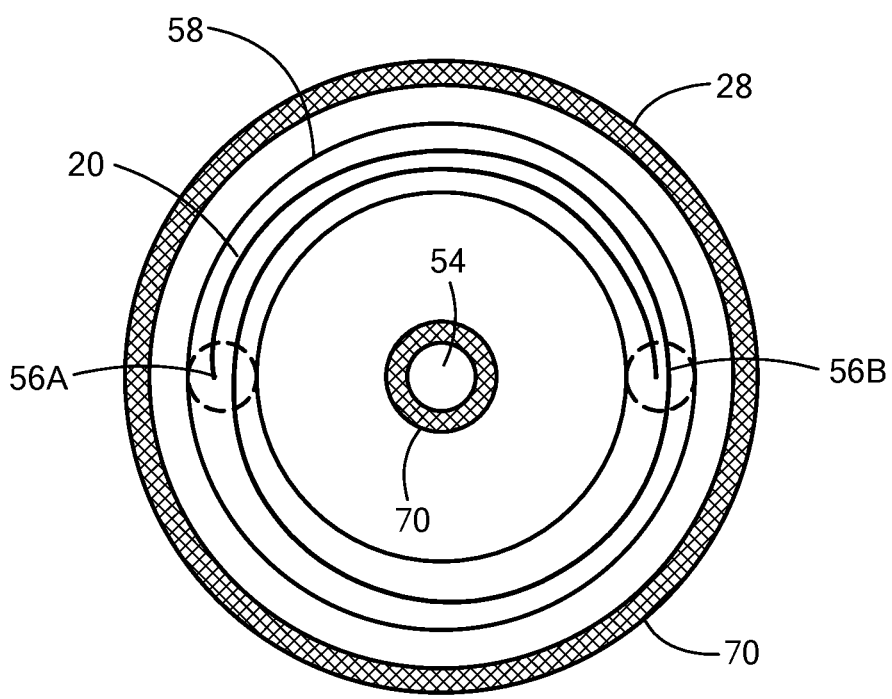
Figure 10:
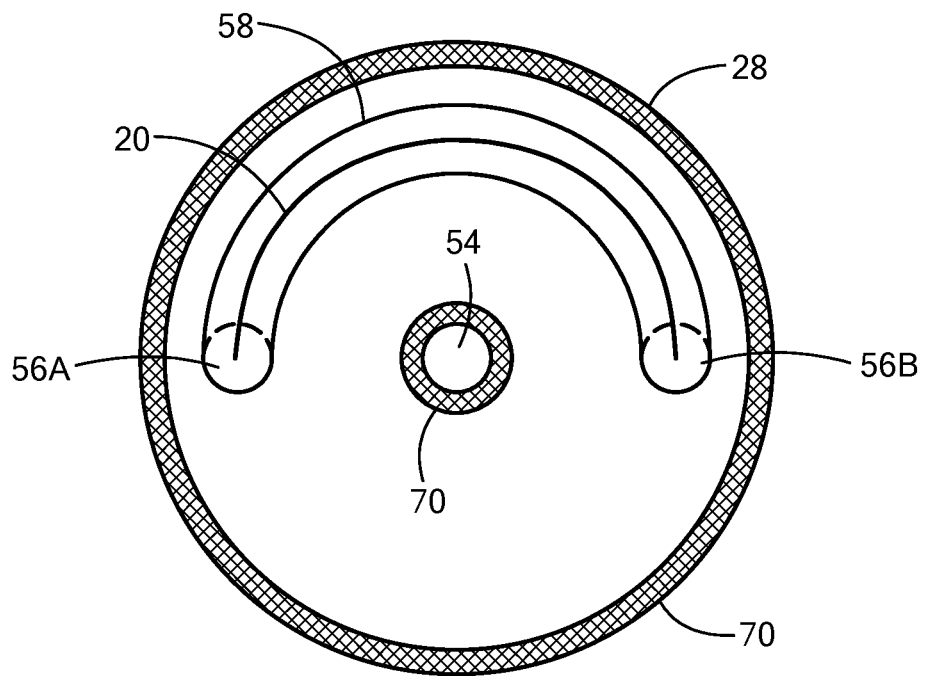

The connecting lumen 58 may form a closed circle containing a crossing point 88 and the pull fiber 20 may pass over itself within at least a portion of the connecting lumen 58 (as shown in FIG. 7). The entirety of the connecting lumen 58 may lie in the same plane, with all portions of the connecting lumen being longitudinally even. Alternatively, the connecting lumen 58 may form an open circle wherein the connecting lumen 58 forms a spiral with certain portions of the connecting lumen 58 being radially separated from each other (as shown in FIG. 8) or one of the two portions of the connecting lumen 58 lies on top of the other, or in spiral configuration in which the two portions of the connecting lumen 58 are radially even but longitudinally separated (as shown in FIG. 9). As another non-limiting embodiment, the connecting lumen 58 may curve around the main lumen 54 in a semicircular shape (as shown in FIG. 10) or include two such connecting portions 58A, 58B each having a semicircular shape extending in opposite directions may be used (as shown in FIG. 11), with two pull fibers 20 in each of pull fiber lumens 56A and 56B, one of which passing through connecting lumen portion 58A and the other passing through connecting lumen portion 58B. Although line 7-7 in FIG. 5 references the cross-sectional view of FIG. 7, the connecting lumen 58 shown in FIG. 5 may generally represent the connecting lumen 58 in any of FIGS. 7-11.

Figure 13A:
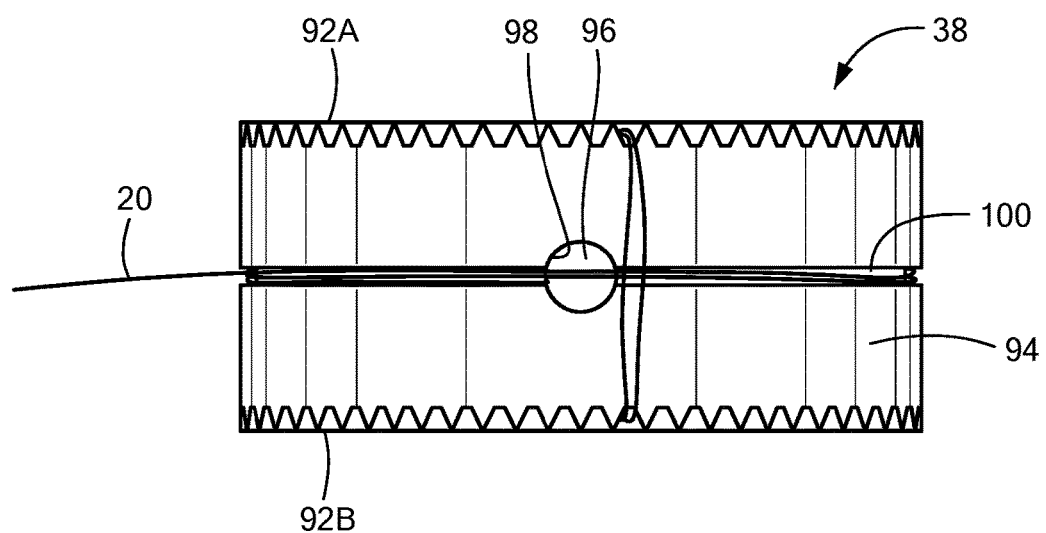
FIGS. 13A and 13B show close-up views of a deflection mechanism.
Figure 13B:
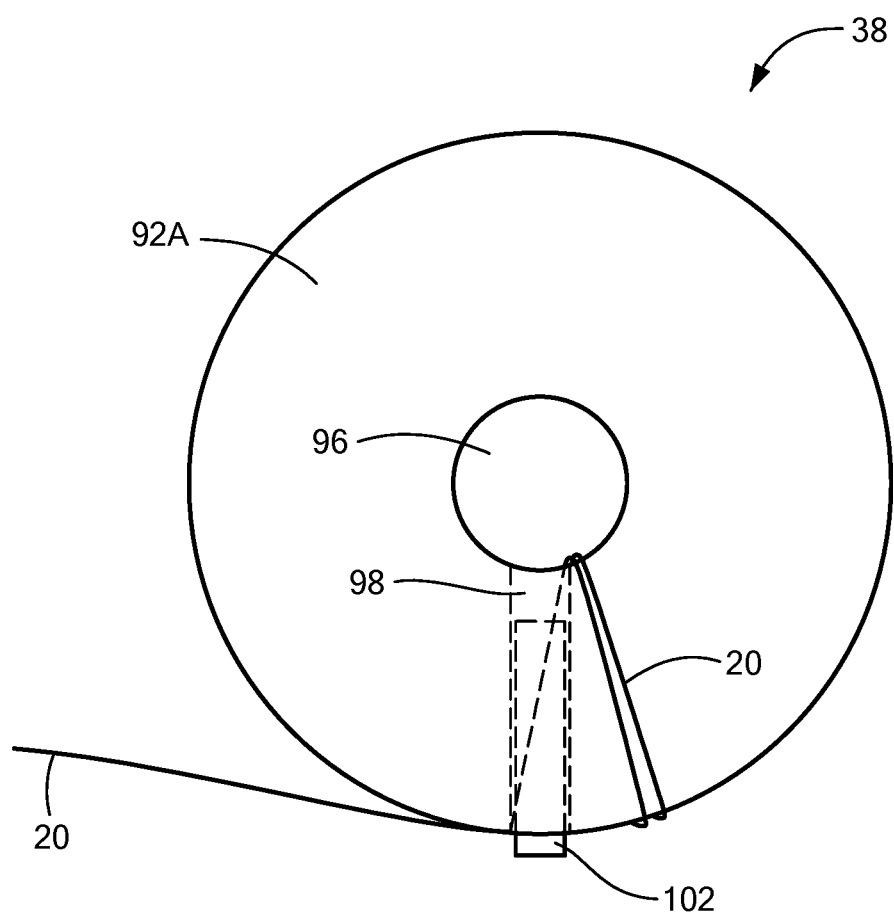

Referring now to FIGS. 13A and 13B, a deflection mechanism is shown. The deflection mechanism 38 may be a spool that is located within the device handle 36 or within or external to the proximal portion 32 of the device 12, and may operate like a pulley to transmit a pull force on the pull fibers 20. For example, the deflection mechanism 38 may be disk-shaped with a first face 92A, a second face 92B, and a curved lateral surface 94, that defines a circumference of the deflection mechanism 38, between the first 92A and second 92B faces. The deflection mechanism 38 may further include a central hole 96 that extends through the first 92A and second 92B faces, a pin hole 98 that extends through the lateral surface 94 to the central hole 96, and a pull fiber channel 100 around the circumference of the deflection mechanism 38. That is, the pull fiber channel 100 may be a channel within the curved lateral surface 94 that extends around at least substantially the entirety of the circumference of the deflection mechanism. Optionally, one or more surfaces of the deflection mechanism 38 may be textured.

To anchor the proximal end of a pull fiber 20 in the deflection mechanism 38, the pull fiber may be positioned within at least a portion of the channel 100, leaving the proximal tail end of the pull fiber free. The tail end of the pull fiber 20 may then be inserted through the pin hole 98 and into the central hole 96, and then wound around the outer surface of the deflection mechanism 38 two times. The pull fiber 20 may then be bonded into place within the pin hole 98 using an adhesive, welding, or bonding agent such as LOCTITE® (Henkel IP & Holding GmbH, Germany). Finally, a non-ferromagnetic metal or polymer pin 102 that is sized and configured to be removably inserted within or coupled to the pin hole 98 may be inserted and bonded into the pin hole 98 to further secure the pull fiber 20. Although the pin 102 is shown in FIG. 13B as partially extending out of the pin hole 98 for illustration, it will be understood that the pin 102 may be completely inserted within the pin hole 98 so that the end of the pin is flush with the inner surface of the channel 100 or the lateral surface 94. Once the proximal portion of the pull fiber 20 is anchored to the deflection mechanism 38, any further rotation of the deflection mechanism 38 will exert or release a pull force on the pull fiber 20. As noted above, the deflection mechanism 38 may be located external to the device handle 36 or may be located within the handle 36 and in mechanical communication with one or more knobs or wheels that the user can operate to deflect the distal end of the device 12.

Other embodiments include:

Embodiment 1

An MRI-compatible medical device, the medical device comprising: an elongate body including a proximal portion and a distal portion; a treatment element at the distal end of the elongate body; a non-ferromagnetic pull fiber; and at least one fiber optic sensor.

Embodiment 2

The medical device of Embodiment 1, wherein the elongate body further includes a first pull fiber lumen, a second pull fiber lumen, and a main lumen.

Embodiment 3

The medical device of Embodiment 2, wherein the elongate body further includes a longitudinal axis, the main lumen being coaxial with the longitudinal axis and the first and second pull fiber lumens being diametrically opposite each other and at least substantially parallel to the central lumen.

Embodiment 4

The medical device of Embodiment 3, wherein the elongate body further includes a connecting lumen that is in communication with the first and second pull fiber lumens, the connecting lumen lying in a plane that is substantially orthogonal to the longitudinal axis.

Embodiment 5

The medical device of Embodiment 4, wherein the connecting lumen is curved around the main lumen.

Embodiment 6

The medical device of Embodiment 5, wherein the pull fiber is composed of a polymer.

Embodiment 7

An MRI-compatible medical device, the medical device comprising: an elongate body including a proximal portion, a distal portion, a longitudinal axis, a main lumen that is coaxial with the longitudinal axis, a first pull fiber lumen that is parallel to the longitudinal axis, a second pull fiber lumen that is parallel to the longitudinal axis, and a connecting lumen that lies in a plane that is at least substantially orthogonal to the longitudinal axis, the first and second pull fiber lumens being diametrically opposite each other, the main lumen being between the first and second pull fiber lumens; a treatment element at the distal end of the elongate body; a non-ferromagnetic pull fiber located within each of the first and second pull fiber lumens; a handle at the proximal end of the elongate body; and a deflection mechanism located within handle and coupled to the pull fiber, the deflection mechanism including a first face, a second face, a rounded lateral wall between the first and second faces, a central hole that extends through the first and second faces, and a pin hole that extends through the lateral surface to the central hole.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support embodiments directed to any such combination or subcombination.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the disclosure.

What is claimed is:

1. An MRI-compatible medical system, the medical system comprising:
   a medical device including:
      an elongate body including a proximal portion, a distal portion, and a distal end, the elongate body further including a first pull fiber lumen, a second pull fiber lumen, a main lumen, and a connecting lumen disposed within the distal portion of the elongate body, the connecting lumen being in communication with the first and second pull fiber lumens, the first and second pull fiber lumens each having a proximal end and a distal end opposite the proximal end, the connecting lumen being curved around the main lumen and defining a loop encircling the main lumen;
      a treatment element disposed at the distal end of the elongate body, the treatment element being distal to the connecting lumen;
      a non-ferromagnetic pull fiber, at least a portion of the pull fiber being disposed within the first pull fiber lumen, the connecting lumen, and the second pull fiber;
      a deflection mechanism coupled to an end of the non-ferromagnetic pull fiber; and
   a console, the console being in fluid communication with the medical device, the medical device not being in electrical communication with the console.

2. The MRI-compatible medical system of claim 1, wherein the elongate body further includes a longitudinal axis, the main lumen being coaxial with the longitudinal axis and the first and second pull fiber lumens being diametrically opposite each other and at least substantially parallel to the main lumen.

3. The MRI-compatible medical system of claim 2, wherein the connecting lumen lies in a plane that is substantially orthogonal to the longitudinal axis.

4. The MRI-compatible medical system of claim 1, wherein the pull fiber is composed of a polymer.

5. The MRI-compatible medical system of claim 1, the medical device further comprising at least one fiber optic sensor.

6. The MRI-compatible medical system of claim 5, wherein the at least one fiber optic sensor is located on a lateral surface of the elongate body.

7. The MRI-compatible medical system of claim 5, wherein the treatment element is an expandable element, the medical device further comprising a shall at least partially disposed within the expandable element.

8. The MRI-compatible medical system of claim 7, wherein the at least one fiber optic sensor is located on the shaft within the expandable element.

9. The MRI-compatible medical system of claim 7, the medical device further comprising an optical multiplexer in communication with the at least one fiber optic sensor.

10. The MRI-compatible medical system of claim 1, wherein the connecting lumen forms a closed circle defining a crossing point for the pull fiber.

11. The MRI-compatible medical system of claim 1, wherein the connecting lumen has a first portion overlapping and spaced apart from a second portion.

12. The MM-compatible medical system of claim 1, wherein the connecting lumen includes at least two connecting lumen portions each having a semicircular shape, the at least two connecting lumen portions being in communication with and extending in opposite circumferential directions between the first and second pull fiber lumens, the at least two connecting lumen portions being curved around the main lumen and cooperating to encircle the main lumen, wherein the pull fiber is a first pull fiber, wherein medical device includes a non-ferromagnetic second pull fiber, and wherein at least a portion of the first pull fiber is disposed within the first pull fiber lumen, one of the at least two connecting lumen portions, and the second pull fiber lumen, and at least a portion of the second pull fiber is disposed within the first pull fiber lumen, the other of the at least two connecting lumen portions, and the second pull fiber lumen.

13. The MM-compatible medical system of claim 1, wherein the deflection mechanism includes:
   a first face;
   a second face opposite the first face;
   a rounded lateral wall between the first and second faces, the rounded lateral wall defining a circumference of the deflection mechanism;
   a pull fiber channel sized and configured to accept at least a portion of the non-ferromagnetic pull fiber, the pull fiber channel being defined circumferentially around the circumference of the deflection mechanism within the rounded lateral wall and disposed between the first face and the second face of the deflection mechanism;
   a central hole extending through the first and second faces; and
   a pin hole defined by the rounded lateral wall and a channel extending from the pin hole to the central hole; and
   wherein another portion of the pull fiber is positioned within at least a portion of the pull fiber channel, the end of the pull fiber being inserted through the pin hole into the central hole, and wound around the first face, the lateral wall, and the second face.

14. The MRI-compatible medical system of claim 13, wherein the deflection mechanism further includes a pin removably insertable within the pin hole.

15. An MRI-compatible medical system, the medical system comprising:
   a medical device comprising:
      an elongate body including a proximal portion; a distal portion, a proximal end, a distal end, a longitudinal axis;
      a treatment element disposed at the distal end of the elongate body;
      a non-ferromagnetic pull fiber having at least a first portion and a second portion, at least the first portion of the pull fiber being in engagement with the distal portion of the elongate body;
      a handle at the proximal end of the elongate body;
      a deflection mechanism located within the handle and coupled to the pill liber, the deflection mechanism including
         a first face, a second face, a rounded lateral wall between the first and second faces, a central hole extending through the first and second faces, a pin hole defined by the rounded lateral wall and a channel extending from the pin hole to the central hole, and a pull fiber channel,
         the pull fiber channel being defined circumferentially around the circumference of the deflection mechanism within the rounded lateral wall and disposed between the first face and the second face of the deflection mechanism,
      wherein the second portion of the pull fiber is positioned within at least a portion of the pull fiber channel, an end of the pull fiber being inserted through the pin hole into the central hole; and wound around the first face, the lateral wall, and the second face; and
   a console, the console being in fluid communication with the medical device, the medical device not being in electrical communication with the console.

16. The MIRI-compatible medical system of claim 15, wherein the deflection mechanism further includes a pin removably insertable within the pin hole.

17. An MRI-compatible medical system, the system comprising:
   a medical device including:
      an elongate body having a proximal portion, a distal portion, and a distal end, the elongate body further including at least two pull fiber lumens, a main lumen, and a connecting lumen with at least two connecting lumen portions disposed within the distal portion of the elongate body; the at least two pull fiber lumens each having a proximal end and a distal end opposite the proximal end, the at least two connecting lumen portions each having a semicircular shape, the at least two connecting lumen portions being in communication with the distal end of each of the at least two pull fiber lumens, the at least two connecting lumen portions extending in opposite circumferential directions between the at least two pull fiber lumens, being curved around the main lumen and cooperating to encircle the main lumen;
      a treatment element disposed at the distal end of the elongate body, the treatment element being distal to the at least two connecting lumen portions;
      a non-ferromagnetic first pull fiber and a non-ferromagnetic second pull fiber, at least a portion of the first pull fiber being disposed within one of the at least two pull fiber lumens, one of the at least two connecting lumen portions, and the other of the at least two pull fiber lumens, at least a portion of the second pull fiber being disposed within the one of the at least two pull fiber lumens, the other of the at least two connecting lumen portions, and the other of the at least two pull fiber lumens;
      a handle coupled to the proximal portion of the elongate body, the handle having an optic multiplexer;
      a deflection mechanism coupled to the handle, the deflection mechanism being coupled to an end of at least one of the first pull fiber and the second pull fiber; and
      at least one fiber optic sensor, the optic multiplexer being in optic communication with the at least one fiber optic sensor;
   a console, the console being in fluid and optical communication with the medical device, the medical device not being in electrical communication with the console; and
   an optic demultiplexer disposed within the console, the optic demultiplexer being in communication with the optic multiplexer.

18. The MRI-compatible medical system of claim 17, wherein the at least two pull fiber lumens are a first and second pull fiber lumen, the elongate body further including:
   a longitudinal axis;
   a main lumen that is coaxial with the longitudinal axis;
   the first pull fiber lumen being at least substantially parallel to the longitudinal axis;

the second pull fiber lumen being diametrically opposite the first pull fiber lumen and at least substantially parallel to the longitudinal axis; and the at least two connecting lumen portions that are in communication with each of the first and second pull fiber lumens, the at least one connecting lumen lying in a plane that is substantially orthogonal to the longitudinal axis.

19. The MRI-compatible medical system of claim 17, wherein the deflection mechanism includes:

a first face;

a second face opposite the first face;

a rounded lateral wall between the first and second faces, the rounded lateral wall defining a circumference of the deflection mechanism;

a pull fiber channel sized and configured to accept at least a portion of the non-ferromagnetic pull fiber, the pull fiber channel being defined circumferentially around the circumference of the deflection mechanism within the rounded lateral wall and disposed between the first face and the second face of the deflection mechanism;

a central hole extending through the first and second faces; and a pin hole defined by the rounded lateral wall and a channel extending from the pin hole to the central hole; and wherein another portion of the at least one of the first pull fiber and the second pull fiber is positioned within at least a portion of the pull fiber channel, the end of the at least one of the first pull fiber and the second pull fiber being inserted through the pin hole into the central hole, and wound around the first face; the lateral wall, and the second face.

20. The MRI-compatible medical system of claim 19, wherein the deflection mechanism further includes a pin removably insertable within the pin hole.

* * * * *